United States Patent [19]

Combs et al.

[11] Patent Number: 5,326,765
[45] Date of Patent: Jul. 5, 1994

[54] 2,2,4-TRIALKYL-1,2-DIHYDROQUINAZOLINE-3-OXIDES

[75] Inventors: Donald W. Combs, Piscataway; Robert Falotico, Belle Mead; Victor Bandurco, Bridgewater, all of N.J.

[73] Assignee: Ortho Pharmaceutical Corporation, Raritan, N.J.

[21] Appl. No.: 789,379

[22] Filed: Nov. 6, 1991

Related U.S. Application Data

[63] Continuation of Ser. No. 479,915, Feb. 14, 1990, abandoned.

[51] Int. Cl.$^5$ ............... A61K 31/505; C07D 403/04
[52] U.S. Cl. ............... 514/259; 514/267; 544/231; 544/283
[58] Field of Search ............... 544/283, 231; 514/250, 514/260

[56] References Cited

U.S. PATENT DOCUMENTS

| 3,398,139 | 8/1968 | Field et al. | 544/283 |
| 3,485,841 | 12/1969 | Field et al. | 544/283 |
| 4,963,554 | 10/1990 | Combs et al. | 544/283 |

FOREIGN PATENT DOCUMENTS

| 403786 | 6/1969 | Australia | 544/283 |

OTHER PUBLICATIONS

Armarego, et al., "Journ. Chem. Soc." C, 1966, pp. 1433–1436.
Walker, et al., "Jour. Org. Chem.", vol. 37, No. 24, 1972 pp. 3755–3770.

*Primary Examiner*—C. Warren Ivy
*Assistant Examiner*—Zinna N. Davis
*Attorney, Agent, or Firm*—Ralph R. Palo

[57] ABSTRACT

Novel 2,2,4-trialkyl-1,2-dihydroquinazoline-3-oxides and their synthesis are described. These compounds possess cardiotonic activity, and are useful for the treatment of heart failure.

18 Claims, No Drawings

2,2,4-TRIALKYL-1,2-DIHYDROQUINAZOLINE-3-OXIDES

This is a continuation of application Ser. No. 07/479,915, filed Feb. 14, 1990 now abandoned.

BACKGROUND OF THE INVENTION

1. Field of the Invention

The present invention relates to novel 2,2,4-trialkyl-1,2-dihydroquinazoline-3-oxides of the formula

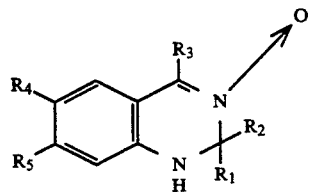

as described further below. These compounds possess cardiotonic activity, and are useful for the treatment of heart failure.

2. Description of the Prior Art

Fey, L. et al., *J. Prakt. Chem.* 35, 225 (1967) describes a 1,2-dihydro-2,4-dialkylquinazoline-3-oxide of the formula

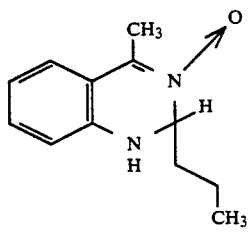

*Chem. Abstract* 62, 16241/E describes similar compounds of the formulas

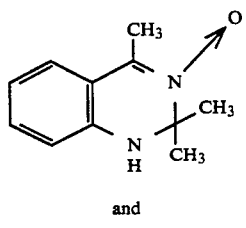

and

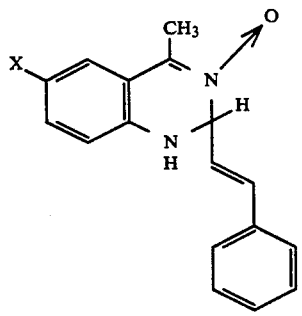

where X is hydrogen or bromo.

Armarego, W.L.F. et. al., *J. Chem. Soc.* 6, 1433 (1966) describes another 1,2-dihydro-2,4-dialkylquinazoline-3-oxide of the formula

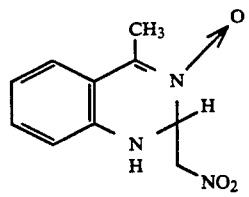

SUMMARY OF THE INVENTION

The present invention is directed to 2,2,4-trialkyl-1,2-dihydroquinazoline-3-oxides of the formula

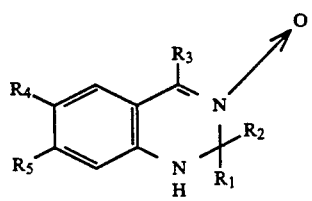

where
$R_1$ and $R_2$ may be the same or different and may be hydrogen, $C_1$-$C_6$ alkyl, $C_1$-$C_6$ hydroxyalkyl, $C_1$-$C_6$ alkoxyalkyl, $C_1$-$C_6$ aryloxyalkyl, $C_1$-$C_6$ carboalkoxyalkyl, or $R_1$ and $R_2$ may form a 5 to 8 membered ring;

$R_3$ may be hydrogen or $C_1$-$C_6$ alkyl; and $R_4$ and $R_5$ may be the same or different and may be hydrogen, $C_1$-$C_6$ alkoxy, methylenedioxy, halogen, methylthio, dialkylamino or heterocyclic amino;

with the proviso that when $R_4$ and $R_5$ are both hydrogen, $R_1$ and $R_2$ cannot both be methyl.

These compounds possess cardiotonic activity, and are useful for the treatment of heart failure.

DETAILED DESCRIPTION OF THE INVENTION

The invention in its broadest aspects relates to 2,2,4-trialkyl-1,2-dihydroquinazoline-3-oxides which have cariotonic activity, and are therefore useful for the treatment of heart failure in mammals. The 2,2,4-trialkyl-1,2-dihydroquinazoline-3-oxide compounds of the invention demonstrating cardiotonic activity are shown in the formula above.

The preferred compounds of the present invention are those wherein:

$R_1$ is hydrogen, $C_1$-$C_6$ alkyl, $C_1$-$C_6$ hydroxyalkyl, $C_1$-$C_6$ carboalkoxyalkyl, or $R_1$ combines with $R_2$ to form a 5 to 8 membered ring;

$R_2$ is hydrogen, $C_1$-$C_6$ alkyl or $R_2$ combines with $R_1$ to form a 5 to 8 membered ring;

$R_4$ is hydrogen, $C_1$-$C_6$ alkoxy, halogen or $R_4$ and $R_5$ together may form a methylenedioxy ring; and $R_5$ is hydrogen, $C_1$-$C_6$ alkoxy or $R_4$ and $R_5$ together may form a methylenedioxy ring.

The 2,2,4-trialkyl-1,2-dihydroquinazoline-3-oxides of the present invention are prepared as shown in the following scheme.

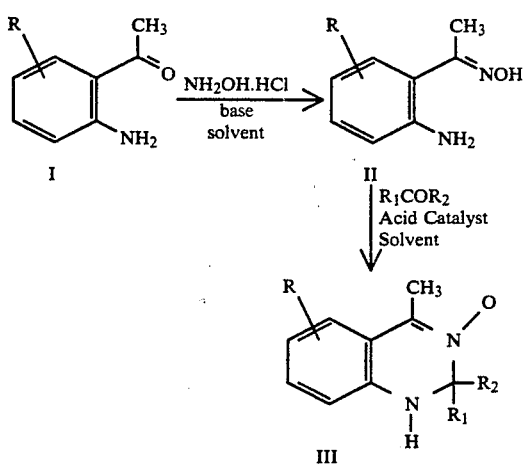

The compounds of the present invention are prepared from aminoacetophenones (I) with the appropriate substitution on the aromatic ring. These compounds are known in the literature. The oximes (II) of these ketones are prepared as described in Kovendi, A. et al., *Chem. Ber.* 98, 1049 (1965) and Simpson, J.C.E. et. al., *J. Chem. Soc.* 646 (1945). In general, a base such as pyridine, sodium hydroxide, or sodium acetate is mixed with a solvent such as water, or an alcohol such as methanol or ethanol. The ketone (I) and hydroxylamine hydrochloride are mixed in this solution and heated to reflux for 1 to 18 hours. Cooling and evaporation of the mixture gives the oximes (II). The quinazoline-3-oxides (III) are then prepared from oximes (II) by suspending or dissolving the oxime in a solvent such as toluene, benzene, or an alcohol such as methanol or ethanol and adding the appropriate ketone($R_1COR_2$) and a catalytic amount of a mineral acid such as sulfuric acid or hydrochloric acid or an organic acid such as *p*-toluenesulfonic acid. The mixture is stirred at temperatures ranging from room temperature to reflux and the product is collected as an insoluble precipitate by filtration after 15 minutes to 2 hours.

Pharmaceutical compositions containing a compound of the present invention as the active ingredient in intimate admixture with a pharmaceutical carrier can be prepared according to convention pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions) or carriers such as starches, sugars, diluents, granulating agents, lubricants, binders disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit (e.g., tablet, capsule, powder, injection, teaspoonful and the like), from about 0.5 to about 100 mg/kg, and preferably from about 1 to about 5 mg/kg of the active ingredient.

The following examples describe the invention in greater particularity and are intended to illustrate but not limit the invention.

EXAMPLE 1

Comparative Example 1,2-Dihydro-2,2,4-trimethylquinazoline-3-oxide

O-Aminoacetophenone oxime (5.5 g, 36.7 mmol) was suspended in 200 ml of benzene, and 20 of acetone was added to the suspension. A spatula-full of *p*-toluenesulfonic acid was then added, and the mixture was stirred at room temperature for 1 hour. The solvent was removed in vacuo, and the residue chromatographed on 600 ml of silica gel eluted with 60:35:5 $CH_2Cl_2$:EtOAc:$CH_3OH$. The fractions containing product were combined, evaporated and recrystallized from ethyl acetate-hexane to give 1.44 g (21%) of the product. m.p 150°–152° C.

Calc for $C_{11}H_{14}N_2O$: C,69.44; H,7.43; N,14.73.

Found: C,69.42; H,7.79; N,14.66

(This compound was reported in the chemical literature *J. Chem. Soc.* 1433 (1966). m.p 149°–150° C.)

EXAMPLE 2

6-Chloro-1,2-dihydro-2,2,4-trimethyl-quinazoline-3-oxide

The title compound was synthesized by the method of Example 1 using 5-chloro-2-aminoacetophenone oxime, but omitting chromatography from ethyl acetate-ether. A 72% yield of the compound was recovered. m.p. 197°–202° C.

Calc for $C_{11}H_{13}Cln_2O$: C,58.78; H,5.84; N,12.47.

Found: C,58.49; H,5.75; N,1208.

EXAMPLE 3

1,2-Dihydro-6,7-methylenedioxy-2,2,4-trimethyl-quinazoline-3-oxide

2-Amino-4,5-methylenedioxyacetophenone oxime (0.644 g, 3.3 mmol) was suspended in 50 ml toluene and 10 ml acetone. A spatula-full of *p*-toluenesulfonic acid was added to the suspension, and the mixture was stirred for 2 hours at room temperature under nitrogen. The solvent was removed in vacuo, and the residue filtered from acetone, and then purified by column chromatography eluted with 10% methanol in $CH_2Cl_2$. The fractions containing product were combined and evaporated, and the residue recrystallized from ethyl acetate-ether to yield 24% of the title compound. m.p 199°–202° C.

Calc for $C_{12}H_{14}N_2O_3$: C,61.52; H,6.04; N,11.96.

Found: C,61.40; H,6.04; N,11.85.

EXAMPLE 4

1,2-Dihydro2,2,4-trimethyl-6,7-dimethoxy-quinazoline-3-oxide

2-Amino-4,5-dimethoxyacetophenone oxime (1.5 g, 7.14 mmol) was suspended in 50 ml benzene and 5 ml acetone. A spatula-full of *p*-toluenesulfonic acid was added to the suspension, and the mixture was stirred at room temperature for 30 minutes. The yellow crystals of the title compound were collected by filtration (94.5%). m.p. 199°–202° C.

Calc for $C_{13}H_{18}N_2O_3$: C,62.37; H,7.26; N,11.18.
Found: C,61.90; H,7.31; N,10.68.

EXAMPLE 5

1,2-Dihydro-2-ethyl-2,4-dimethyl-6,7-dimethoxyquinazoline-3-oxide

The title compound was synthesized as in Example 4 using 2-butanone instead of acetone resulting in a 92% yield of 1,2-dihydro-2-ethyl-2,4-dimethyl-6,7-dimethoxyquinazoline-3-oxide. m.p. 180°–182° C.

Calc for $C_{14}H_{20}N_2O_3$: C,63.54; H,7.64; N,10.59.
Found: C,63.14; H,7.57; N,10.14.

EXAMPLE 6

1,2-Dihydro-2-isopropyl-2,4-dimethyl-6,7-dimethoxyquinazoline-3-oxide

The title compound was synthesized by the method of Example 4 using 3-methyl-2-butanone instead of acetone, and heating the reaction mixture of 60° C. after 12 hours at room temperature. Filtration and recrystallization from ethanol-ethyl acetate-hexane gave 48% of the product. m.p. 198°–200° C.

Calc for $C_{15}H_{22}N_2O_3$: C,64.71; H,7.48; N,10.07.
Found: C,64.56; H,7.87; N,9.83.

EXAMPLE 7

1,2-Dihydro-2,4-dimethyl-2-(2-carboethoxyethyl)-6,7-dimethoxyquinazoline-3-oxide The title compound was synthesized by the method of Example 4 using ethyl levulinate and heating to 100° C. in toluene for 7 hours. The solvent was removed in vacuo and the resultant oil recrystallized from ethyl acetate to yield 70% of the title compound. m.p. 172°–174° C.

Calc for $C_{17}H_{24}N_2O_5$: C,60.69; H,7.21; N,8.33.
Found: C,60.39; H,7.55; N,8.09.

EXAMPLE 8

1,2-Dihydro-2,4-dimethyl-6,7-dimethoxy-2-phenoxymethylquinazoline-3-oxide

The title compound was synthesized by the method of Example 3 using phenoxy-2-propanone instead of acetone, and stirring for 2 days. There was a 70% recovery of the title compound after chromatography and recrystallization from ethyl acetate-ether-hexane. m.p. 145°–146° C.

Calc for $C_{19}H_{22}N_2O_4$: C,66.64; H,6.49; N,8.18.
Found: C,66.62; H,6.50; N,8.10.

EXAMPLE 9

1,2-Dihydro-2,2-diethyl-4-methyl-6,7-dimethoxyquinazoline-3-oxide

The title compound was synthesized by the method of Example 4 using 3-pentanone instead of acetone, and heating to 100° C. after stirring at room temperature overnight. Filtration and recrystallization from ethyl acetate-ethanol gave 51% of the product. m.p. 195°–197° C.

Calc for $C_{15}H_{22}N_2O_3$: C,64.71; H,7.98; N,10.07.
Found: C,64.53; H,8.18; N,9.98.

EXAMPLE 10

Spiro[1,2-dihydro-6,7-dimethoxy-4-methylquinazoline-3-oxide-2,1'-cyclopentane]

2-Amino-4,5-dimethoxyacetophanone oxime (1.0 g, 4.76 mmol) was suspended in 35 ml toluene, and cyclopentanone (0.42 ml, 4.76 mmol) was added, followed by 10 mg of p-toluenesulfonic acid. The mixture was stirred at 55° C. for 24 hours. The resultant solid was collected by filtration and recrystallized from ethyl acetate-ethanol (39% yield). m.p. 225°–227 C.

Calc for $C_{15}H_{20}N_2O_3$: C,65.18; H,7.31; N,10.14.
Found: C,64.78; H,7.21; N,10.03.

EXAMPLE 11

Spiro[1,2-dihydro-4-methylquinazoline-3-oxide-2,1'-cyclopentane]

The title compound was synthesized by the method of Example 10 using o-aminoacetophenone oxime instead of the dimethoxy oxime to yield 44% of spiro[1,2-dihydro-4-methylquinazoline-3-oxide-2,1'-cyclopentane]. m.p. 175°–177° C.

Calc for $C_{13}H_{16}N_2O$: C,72.17; H,7.47; N,12.95.
Found: C,72.50; H,7.57; N12.94.

EXAMPLE 12

Spiro[1,2-dihydro-6-chloro-4-methylquinazoline-3-oxide-2,1'-cyclopentane]

The title compound was synthesized by the method of Example 10 using 5-chloro-2-aminoacetophenone oxime instead of the dimethoxy oxime. The resultant product yield was 55%. m.p. 143°–144.5° C.

Calc for $C_{13}H_{15}ClN_2O$: C,62.25; H,6.04; N,11.7.
Found: C,62.52; H,6.06; N,10.98.

EXAMPLE 13

1,2-Dihydro-4-methyl-6,7-dimethoxyquinazoline-3-oxide

2-Amino-4,5-dimethoxyacetophenone oxime (4.7 g, 22.4 mmol) was suspended in 200 ml of benzene. Paraformaldehyde (738 mg, 1 equivalent) was then added, followed by 135 mg of p-toluenesulfonic acid. The mixture was refluxed with removal of water (Dean-Stark trap) for 12 hours. Then the residue after solvent removal was suspended in ethyl acetate, filtered and washed with hexane to give 4.5 of product (90%). m.p. 161°–163° C. Mass Spectrum M+ 222 (theoretical 222).

NMR 6.87(1, S, ArH); 640(1, S, ArH);
4.80(2, m, $CH_2$, J-6Hz); 3.80(3, S, OMe);
3.78(3, S, OMe); 2.40(3, S, $CH_3$)

EXAMPLE 14

1,2-Dihydro-6,7-dimethoxy-2-(4-hydroxybutyl)-4-methylquinazoline-3-oxide

2-Amino-4,5-dimethoxyacetophenone oxime (3 g) was suspended in 20 ml of dihydropyran and 25 mg of p-toluenesulfonic acid. The suspension was heated to 40° C. and stirred overnight. Excess dihydropyran was removed in vacuo, and the residue crystallized from methanolwater to give 0.65 g (15%) of product. m.p. 143°–144.5° C.

Calc for $C_{15}H_{22}N_2)_4$: C,61.19; H,7.55; N,9.52.
Found: C,61.06; H,7.50; N,9.26.

EXAMPLE 15

1,2-Dihydro-6,7-methylenedioxy-2,4-dimethyl-quinazoline-3-oxide

The title compound was synthesized by the method of Example 4 using 6-aminopiperonal oxime instead of the dimethoxy oxime. The resultant product yield was 99%. m.p. 105°–107° C. Mass spectrum M+ 200 (theoretical 220).

EXAMPLE 16

Spiro[1,2-dihydro-4-methylquinazoline-3-oxide-2,1'-(4-carboethoxy)-4-azacyclohexanone]

The title compound was synthesized by the method of Example 10 using o-aminoacetophenone oxime and 4-carboethoxy-4-azacyclohexanone. The resultant product yield was 80.5%. m.p. 156°–159° C.

Calc for $C_{16}H_{21}N_3O_3$: C,63.33; H,6.98; N,13.85.
Found: C,63.27; H,7.01; N,13.71.

EXAMPLE 17

Acute In Vivo Cardiotonic Evaluation

Using the procedures adapted from Alousi, A.A. et al., *J. Circ. Res.* 45, 666 (1979), adult mongrel dogs were anesthetized with sodium pentobarbital, and artificially respirated. Arterial pressure was recorded via a femoral artery and the pressure pulse used to trigger a cardiotachometer for heart rate. Left ventricular pressure was measured with a Millar catheter, and dP/dt was derived. Cardiac output was determined by measuring ascending aortic blood flow with an electromagnetic flow probe, and myocardial contractile force (CF) was measured with a Walton Brodie strain gauge sutured to the right ventricle. Lead II EKG was also recorded.

A standard dose of dopamine was administered in order to assess myocardial inotropic responsiveness. Example compounds were then administered by i.v. infusion and the effects on cardiovascular parameters were determined. The dose of each example compound was 1.875 mg/kg.

The dose related effects of the example compounds on myocardial contractile force were compared to pretreatment control values, expressed as a% change and rated for activity.

The results of the procedure are shown below in Table 1.

TABLE 1

| Example | % Increase In Myocardial Contractile Force @ 1.875 mg/kg. |
| --- | --- |
| 4 | 98 |
| 5 | 60 |
| 7 | 56 |

What is claim is:

1. A compound of the formula I:

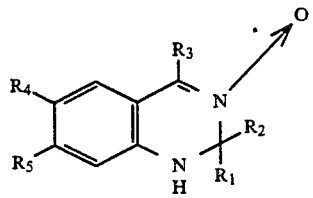

where $R_1$ $R_2$ are the same or different and are hydrogen, $C_1$–$C_6$ alkyl, $C_1$–$C_6$ hydroxyalkyl, carboethoxyethyl or $R_1$ and $R_2$ together form a 5 to 8 membered ring;

$R_3$ is hydrogen or $C_1$–$C_6$ alkyl; and $R_4$ and $R_5$ are the same or different and are hydrogen, $C_1$–$C_6$ alkoxy, methylenedioxy, halogen, methylthio or dialkylamino;

with the proviso that when $R_4$ and $R_5$ are both hydrogen, $R_1$ and $R_2$ cannot both be methyl;

with the proviso that when $R_4$ and $R_5$ are both H, $R_3$ is methyl, $R_1$ and $R_2$ can not be the combination of H and propyl.

2. The compound of claim 1 wherein $R_1$ is hydrogen, $C_1$–$C_6$ alkyl, $C_1$–$C_6$ hydroxyalkyl, carboethoxyethyl;

$R_2$ is hydrogen, $C_1$–$C_6$ alkyl, or $R_1$ or $R_2$ may form a 5 to 6 membered ring;

$R_4$ is hydrogen, $C_1$–$C_6$ alkoxy, halogen or $R_4$ and $R_5$ together may form a methylenedioxy ring; and $R_5$ is hydrogen, $C_1$–$C_6$ alkoxy or $R_4$ and $R_5$ together may form a methylenedioxy ring.

3. The compound of claim 1 selected from the group consisting of 6-chloro-1,2-dihydro-2,2,4-trimethyl-quinazoline-3-oxide, 1,2-dihydro-6,7-methylenedioxy-2,2,4-trimethylquinazoline-3-oxide, 1,2-dihydro-2,2,4-trimethyl-6,7-dimethoxyquinazoline-3-oxide, 1,2-dihydro-2-ethyl-2,4-dimethyl-6,7-dimethoxyquinazoline-3-oxide, 1,2-dihydro-2-isopropyl-2,4-dimethyl-6,7-dimethoxyquinazoline-3-oxide, 1,2-dihydro-2,2-diethyl-4-methyl-6,7-dimethoxyquinazoline-3-oxide, 1,2-dihydro-4-methyl-6,7-dimethoxyquinazoline-3-oxide and 1,2-dihydro-6,7-methylenedioxy-2,4-dimethylquinazoline-3-oxide.

4. The compound of claim 1 selected from the group consisting of 1,2-dihydro-2,4-dimethyl-2-(2-carboethoxyethyl)-6,7-dimethoxyquinazoline-3-oxide and spiro[1,2-dihydro-4-methylquinazoline-3-oxide-2,1'-(4-carboethoxy)-4-azacyclohexanone].

5. The compound of claim 1 selected from the group consisting of 1,2-dihydro-2,4-dimethyl-6,7-dimethoxy-2-phenoxymethylquinazoline-3-oxide and 1,2-dihydro-6,7-dimethoxy-2-(4-hydroxybutyl)-4-methylquinazoline-3-oxide.

6. The compound of claim 1 selected form the group consisting of spiro[1,2-dihydro-6,7-dimethoxy-4-methylquinazoline-3-oxide-,1'cyclopentane], spiro[1,2-dihydro-4-methylquinazoline-3-oxide-2,1'-cyclopentane] and spiro[1,2-dihydro-6-chloro-4-methylquinazoline-3-oxide-2,1'-cyclopentane].

7. A pharmaceutical composition comprising as an active ingredient an effective amount of the compound of claim 1 and a suitable pharmaceutical carrier.

8. A pharmaceutical composition comprising as an active ingredient an effective amount of the compound of claim 2 and a suitable pharmaceutical carrier.

9. A pharmaceutical composition comprising as an active ingredient an effective amount of the compound of claim 3 and a suitable pharmaceutical carrier.

10. A pharmaceutical composition comprising as an active ingredient an effective amount of the compound of claim 4 and a suitable pharmaceutical carrier.

11. A pharmaceutical composition comprising as an active ingredient an effective amount of the compound of claim 5 and a suitable pharmaceutical carrier.

12. A pharmaceutical composition comprising as an active ingredient an effective amount of the compound of claim 6 and a suitable pharmaceutical carrier.

13. A method of treating heart failure in mammals by administering an effective amount of the compound of claim 1.

14. A method of treating heart failure in mammals by administering an effective amount of the compound of claim 2.

15. A method of treating heart failure in mammals by administering an effective amount of the compound of claim 3.

16. A method of treating heart failure in mammals by administering an effective amount of the compound of claim 4.

17. A method of treating heart failure in mammals by administering an effective amount of the compound of claim 5.

18. A method of treating heart failure in mammals by administering an effective amount of the compound of claim 6.

* * * * *